(12) United States Patent
Yarosh et al.

(10) Patent No.: US 11,369,564 B2
(45) Date of Patent: Jun. 28, 2022

(54) WATERY LOTION SKIN CARE COMPOSITIONS AND METHODS

(71) Applicant: ELC Management LLC, Melville, NY (US)

(72) Inventors: Daniel B. Yarosh, Merrick, NY (US); Thomas Mammone, Farmingdale, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 147 days.

(21) Appl. No.: 16/711,675

(22) Filed: Dec. 12, 2019

(65) Prior Publication Data
US 2020/0113815 A1 Apr. 16, 2020

Related U.S. Application Data

(62) Division of application No. 14/497,711, filed on Sep. 26, 2014, now abandoned.

(60) Provisional application No. 61/884,599, filed on Sep. 30, 2013.

(51) Int. Cl.
| *A61K 8/99* | (2017.01) |
| *A61Q 19/00* | (2006.01) |
| *A61Q 19/08* | (2006.01) |
| *A61K 8/96* | (2006.01) |

(52) U.S. Cl.
CPC ............... *A61K 8/99* (2013.01); *A61K 8/965* (2013.01); *A61Q 19/00* (2013.01); *A61Q 19/08* (2013.01); *A61K 2800/5922* (2013.01); *A61K 2800/85* (2013.01); *A61K 2800/884* (2013.01)

(58) Field of Classification Search
None
See application file for complete search history.

(56) References Cited

PUBLICATIONS

Raskin et al. (2004) Current Pharmaceutical Design 10, 3419-3429. (Year: 2004).*
Revilla et al. (1998) J. Agric. Food Chem. 46, 4592-4597. (Year: 1998).*
Tallarida (2011) Genes and Cancer, 2(11): 1003-1008. (Year: 2011).*

* cited by examiner

*Primary Examiner* — Russell G Fiebig
(74) *Attorney, Agent, or Firm* — Yonggang Wu

(57) ABSTRACT

A watery lotion composition for topical application to skin comprising at least one extract from the fermentation of the microorganism *Bifidobacterium*, at least one extract from the fermentation of the microorganism *Lactobacillus*, and mineral water having at least 250 ppm of total mineral dissolved solids and a method for improving the efficacy of a watery lotion and/or a second skin care product by layering the products on the skin.

10 Claims, 3 Drawing Sheets

WATERY LOTION SKIN CARE COMPOSITIONS AND METHODS

CROSS-REFERENCE TO RELATED APPLICATIONS

The present application is a Divisional Application of U.S. Non-Provisional application Ser. No. 14/497,711, filed on Sep. 26, 2014, which claims priority from U.S. Provisional Application No. 61/884,599, filed on Sep. 30, 2013. The entire contents of each of the above are incorporated herein by reference.

TECHNICAL FIELD

The invention is in the field of skin care compositions and regimens for treating skin, and more particularly, skin care compositions in the serum or watery lotion category and regimens for improving efficacy of individual products when they are layered onto the skin.

BACKGROUND OF THE INVENTION

Skin care products referred to as watery lotions are very popular, particularly with Asian skin care consumers. Watery lotions are generally considered to be lotions or serums with no, or a very insignificant oily phase. Most watery lotions contain water at greater than about 85%, or even greater than 90% by weight of the total composition. While the benefits of watery lotion include the light fresh feel of applying mostly water to skin, the disadvantage is that the high water content prevents inclusion of many skin benefit active ingredients that are compatible with, and can only be incorporated into compositions with a significant oil phase. Thus, the need gap is to formulate watery lotions having maximum effectiveness in treating skin while at the same time maintaining the high water content.

Also of interest is enhancing the effectiveness of watery lotions, not only through formulation, but using regimens where the watery lotion and one or more additional products are layered onto the skin to optimize efficacy without causing inhibitory activity. More specifically, the efficacy of watery lotions can be maximized by combining with skin care serums, especially those containing extracts from fermentation products of microorganisms such as *Lactobacillus* or *Bifidobacterium*.

It has been discovered that formulating watery lotions with a certain combination of ferments and mineral containing water with mineral concentrations greater than what is found in de-ionized water and, in some cases, similar to what is found in blood, provides compositions with maximum effectiveness.

In addition, it has been discovered that the efficacy of watery lotions in providing skin benefits can be improved by layering of two or more products onto the skin, one of which is the watery lotion of the invention and the other being a skin care serum, cream, or lotion, preferably containing at least one extract from the fermentation of a microorganism from *Lactobacillus* or *Bifidobacterium* genus.

SUMMARY OF THE INVENTION

The invention is directed to a watery lotion composition for topical application to skin comprising an extract from the fermentation of a probiotic microorganism from *Bifidobacterium* or *Lactobacillus* genus and mineral water having at least 250 ppm of total mineral dissolved solids.

The invention is directed to a regimen for improving the efficacy of watery lotion and/or a second skin care product by layering onto the skin a watery lotion that contains an extract from the fermentation of a microorganism from the *Bifidobacterium* or *Lactobacillus* genus; and a second skin care product preferably also containing at least one extract from the fermentation of a probiotic microorganism from the *Bifidobacterium* or *Lactobacillus* genus. The efficacies that may be improved include, but are not limited to, balanced cellular renewal, skin where the basal proliferative and epidermal differentiating layers are balanced to provide healthy, youthful skin, improved water retention, and as further set forth herein.

The invention is also directed to a skin surface comprised of a basal layer, an epidermal layer, a layer formed from application of a watery lotion composition containing at least one extract from the fermentation of a probiotic microorganisms from the *Bifidobacterium* or *Lactobacillus* genus; and a layer formed from application of a skin care product containing at least one extract from the fermentation of a probiotic microorganisms from the *Bifidobacterium* or *Lactobacillus* genus; wherein the compositions layered onto the skin cause the basal cells in the basal layer of the skin and the epidermal cells in the epidermal layer of the skin to exhibit balanced proliferative and differentiating activity respectively.

DETAILED DESCRIPTION

Figure 1:
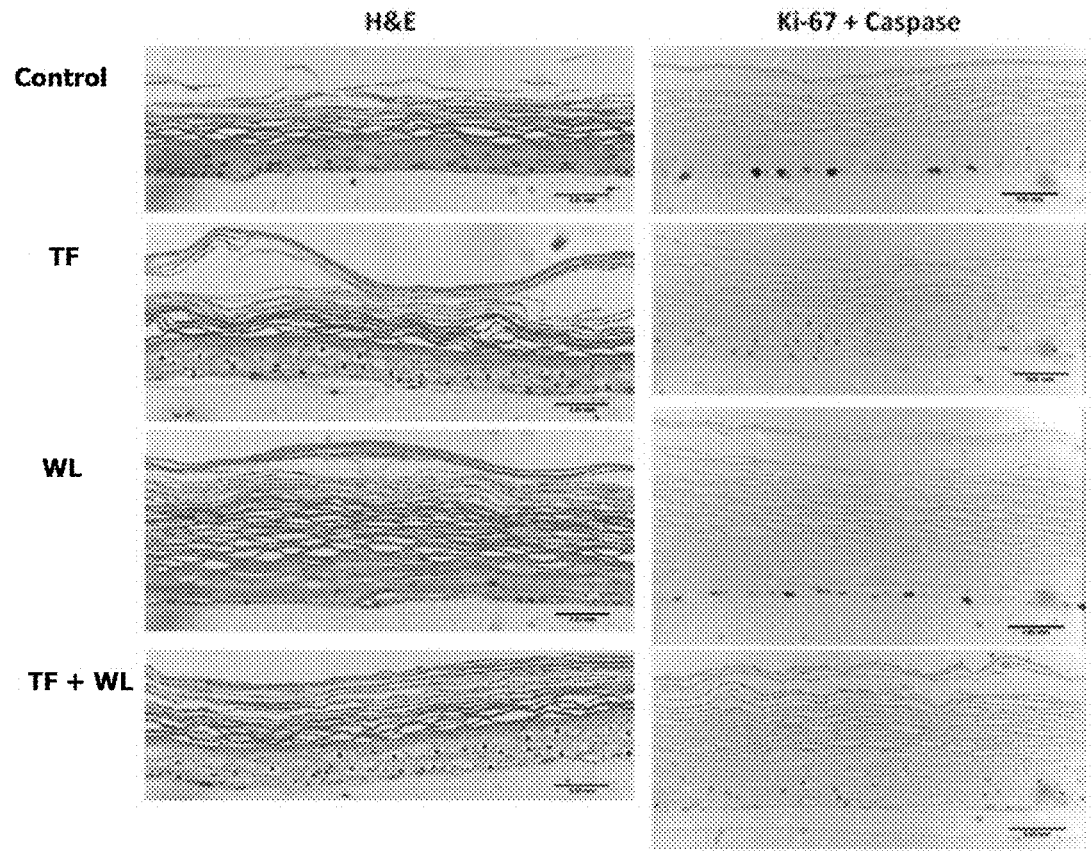
FIG. 1: depicts histological sections of skin stained with hematoxylin & eosin (H&E), Ki-67 protein and Caspase 3 using two separate antibodies. Ki-67 indicates proliferation and Caspase 3 indicates apoptosis. The amount of basal cell proliferation and epidermal differentiation was shown in skin sections that are untreated, treated with a watery lotion, treated with a second skin care product alone, and treated with both products. The results show that skin sections treated with watery lotion and the second skin care product show balanced skin renewal where the new cell generation (or proliferation) in the basal layer and the cellular differentiation in the epidermal layer are balanced. Where cellular proliferation and differentiation in basal and epidermal layers is balanced, skin is most healthy, normalized and exhibits excellent integrity.

All percentages mentioned herein are percentages by weight unless otherwise indicated.

The term "watery lotion" means an aqueous based composition having from about 75-99% by weight of the total composition of water.

The term "mineral water" means water having at least 250 ppm of total mineral dissolved solids.

I. The Watery Lotion Composition

A. Mineral Water

The watery lotion composition of the invention comprises at least about 80%, more preferably from about 80 to 99.9% by weight of water. The water portion may comprise from 0.01 to 100%, preferably from 0.05 to 25%, more preferably from about 0.1 to 20% by weight of the total water portion, of mineral water having at least 250 ppm of total dissolved mineral solids. In one preferred embodiment the mineral water comprises concentrations of dissolved mineral solids including but not limited to aluminum, antimony, barium, beryllium, bismuth, boron, bromine, cadmium, calcium, carbon, cerium, cesium, chloride, chromium, cobalt, copper, dysprosium, erbium, europium, fluoride, gadolinium, gallium, germanium, gold, hafnium, homium, indium, iodine, iridium, iron, lanthanum, lithium, lutetium, magnesium manganese, molybdenum, neodymium, niobium, osmium, palladium, phosphorus, platinum, potassium, praseodymium, rhenium, rhodium, rubidium, ruthenium, samarium, scandium, selenium, silicon, silver, sodium, strontium, sulfur, tantalum, tellurium, terbium, thallium thordium, thulium, tin, titanium, tungsten, vanadium, ytterbium, yttrium, zinc, zirconium. In another preferred embodiment, the mineral water has a pH ranging from 2.5 to 4.3, preferably from 2.6 to 3.9 and a specific gravity of 1.0 to 1.03. A suitable mineral water may be purchased from TRC Nutritional Laboratories under the trade name 77LPPM TRC Minerals.

B. Extract from Probiotic Microorganism

1. Extract from *Lactobacillus* genus

The watery lotion composition may comprise at least one extract, preferably in the form of a ferment or ferment lysate obtained by fermenting a microorganism from *Lactobacillus*. Examples of the *Lactobacillus* genus include, but are not limited to, *plantarum, casei, crispatus*, etc. The ferment may be in the form of a lysate, filtrate, or both. In the case of a lysate, the fermentation product is lysed. In the case of a filtrate, the fermentation product is filtered. The ingredients may be purchased from Active Concepts under the tradename AC Probiotic 1; Natural F&P Co. Ltd under the tradename *Lactobacillus crispatus* KLB46; RNA Co. under the trade name K-LAC. The ingredient may also be purchased in the form of mixtures with other ingredients or probiotic organisms.

The ferment may be present in amounts ranging from about 0.001 to 10%, preferably from about 0.1 to 5%, more preferably from about 0.1 to 3%.

2. Extract from *Bifidobacterium* genus

The composition also comprises at least one extract, preferably in the form of a ferment or ferment lysate from the *Bifidobacterium* genus. Examples include *Bifida* ferment extract, *Bifida* ferment lysate, or *Bifida* ferment filtrate. The fermentation extract of *Bifida* may also be in the form of mixtures with other ingredients or probiotic microorganisms. The *Bifidobacterium* fermentation product may be present in the composition in amounts ranging from about 0.01 to 10%, preferably from about 0.05 to 5%, more preferably from about 0.1 to 2%.

C. Other Ingredients

The watery lotion may also contain other ingredients including botanically derived actives, peptides, humectants, surfactants, and preservatives.

1. Peptides

Examples of suitable peptides including those having beneficial effects on skin are acetylated peptides, such as Acetyl hexapeptides followed by numbers ranging from 1 to 49 including all whole integers in between. Preferred is Acetyl hexapeptide-8 (sold under the tradename Argireline®). Also suitable are palmitoylated peptides such as Palmitoyl oligopeptides, Palmitoyl pentapeptides, Palmitoyl hexapeptides, Palmitoyl tetrapeptides, Palmitoyl tripeptides. Other suitable peptides are described in the *C.T.F.A. International Cosmetic Ingredient Dictionary and Handbook*, 11$^{th}$ Edition, 2006. If present, the peptides may range from about 0.0001 to 3%, preferably from about 0.0005 to 2.5%, more preferably from about 0.001 to 1%.

2. Humectants

The composition may also comprise one or more humectants. If present, they may range from 0.01 to 10%, preferably from 0.05 to 8%, more preferably from about 0.1 to 7%. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, polysachharides, and so on. Also suitable are urea and/or hyaluronic acid. Preferably, the humectants used in the composition of the invention are $C_{1-6}$, preferably $C_{2-4}$ alkylene glycols, most particularly butylene glycol.

3. Surfactants

The composition may contain one or more surfactants. Preferred are nonionic organic surfactants such as alkylene glycols, alkoxylated alcohols, or ethers, formed by the reaction of an alcohol with an alkylene oxide, usually ethylene or propylene oxide. Preferably the alcohol is either a fatty alcohol having 6 to 30 carbon atoms.

Examples of alkylene glycols, specifically ethylene or propylene glycols having from about 1 to 200 repeating EO or PO units, including all whole integers from 1 to 200. More preferred are polyethylene glycols (PEG) having from 2 to 100 repeating units, for example PEG 1-200 including all whole integers in between. More specifically are PEG where the number of repeating ethylene oxide units ranges from 40-75. Specific examples include PEG-60, PEG-75 is preferred.

Examples of such ingredients include Steareth 2-100, which is formed by the reaction of stearyl alcohol and ethylene oxide and the number of ethylene oxide units ranges from 2 to 100 including all whole integers in between; Oleth 2-100, which is formed by the reaction of oleyl alcohol and ethylene oxide; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Also suitable are polyethylene glycols of glycerin or glucose such as Glycereth 2-100, gluceth 2-100 including all whole integers in between.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Also suitable are various types of betaine surfactants. Such surfactants may be present in amounts ranging from about 0.01 to 25%, preferably from about 0.05 to 20%, more preferably from about 0.1 to 15% by weight of the total composition.

4. Viscosity Modifiers

The composition may also contain one or more ingredients that increase the viscosity of the composition. If present, ranges are from about 0.01 to 10%, preferably from about 0.05 to 8%, more preferably from about 0.1 to 5% by weight of the total composition. Examples include synthetic polymeric thickening agents such as carbopol, C10-30 alkyl acrylates crosspolymer, acrylates copolymer, and ammonium acryloyldimethyltaurate/beheneth-25 copolymer, sodium acryloyldimethyl taurate/VP copolymer, ammonium acryloyldimethyltaurate copolymer and those sold by Clariant under the Aristoflex® trademark.

5. Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, thermus thermophilis ferment extract, camelina sativa seed oil, *Boswellia serrata* extract, olive extract, *Arabidopsis thaliana* extract, *Acacia dealbata* extract, *Acer saccharinum* (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officianalis, Citrus medica limonum, Panax ginseng, Siegesbeckia orientalis, Fructus mume, Ascophyllum nodosum, Bifida* Ferment lysate, *Glycine soja* extract, *Beta vulgaris, Haberlea rhodopensis, Polygonum cuspidatum, Citrus aurantium dulcis, Vitis vinifera, Selaginella tamariscina, Humulus lupulus, Citrus reticulata* peel, *Punica granatum, Asparagopsis armata, Curcuma longa, Menyanthes trifoliata, Helianthus annuus, Hordeum vulgare, Cucumis sativus, Evernia prunastri, Evernia furfuracea,* and mixtures thereof.

II. The Method

The invention is directed to a regimen for improving the efficacy of watery lotion and/or a second skin care product also applied to skin. More specifically, the watery lotion contains an extract from the fermentation of a probiotic microorganism from the *Bifidobacterium* or *Lactobacillus* genus; and a second skin care product may also containing at least one extract from the fermentation of a probiotic microorganism from the *Bifidobacterium* or *Lactobacillus* genus.

The efficacy that is improved includes balanced skin renewal between basal and epidermal skin layers (where cellular proliferation in the basal layer and cellular differentiation in the epidermal layer are balanced), improved skin integrity, improved skin barrier properties, improving overall skin health, normalizing skin, and improving moisturization by causing increased water retention in skin. Preferably, the balanced skin renewal causes a proliferation to differentiation ratio in the basal to epidermal layers of skin that ranges from about 30-70% proliferation and 30-70% differentiation. More preferred is where the proliferation to differentiation ratio in the basal to epidermal layers ranges from 40-60% proliferation to 60-40% differentiation. Most preferred is where the proliferation to differentiation ratio in the basal to epidermal layers of skin is about 50% proliferation and about 50% differentiation. This provides optimal skin integrity, healthy and viability. In addition, since the proliferative activity of cells in the basal layer decreases with age, treatment according to the regiment of the invention will cause improved proliferative activity and ensure that the proliferative activity is balanced with cellular differentiation in the epidermal layer to most closely approximate the health and viability of youthful skin.

The second skin care product may be in the form of a cream, lotion, or serum. In one preferred embodiment the second skin care product is in the form of a serum comprising from about 20-99% water, and from about 0.1-20% one or more surfactants, and optionally, about 0.1-20% of one or more oils, and optionally 0.1-10% of one or more peptides, botanical extracts, viscosity modifiers, humectants, etc. as set forth above with respect to the watery lotion. Preferred is where the serum comprises, from about 20-99% water, 0.1-10% surfactants, 0.1-5% oil, 0.1-3% extract from probiotic microorganism, preferably *Bifidobacterium;* 0.1-10% of one or more humectants. More preferred is where the skin care product is in the form of a serum comprising:

20-99% water, 0.1-5% one or more surfactants selected from alkylene glycols such as ethylene or propylene glycols; alkoxylated glucose, alkoxylated alcohols, glyceryl esters; glyceryl ethers, or mixtures thereof, 0.1-3% extract from probiotic microorganisms selected from *Lactobacillus* genus, *Bifidobaceterium* genus, or mixtures thereof, 0.1-10% of humectants selected from polyhydric alcohols, alkylene glycols or glycerin, butylene glycol, hexylene glycol, or mixtures thereof, More preferred is where the skin care product comprises:

20-99% water, 0.1-5% one or more surfactants selected from polyethylene glycols having from 40-100 repeat ethylene oxide units; polypropylene glycols having from 3 to 100 repeat propylene glycol units; polyethylene/polypropylene glycols having from about 40-100 repeat ethylene glycol units and 3-100 repeat propylene glycol units; $C_{12-40}$ straight or branched chain, saturated or unsaturated alkoxylated alcohols; polyethylene glycols of glycerin; polyethylene glycols of glucose or methyl glucose; polyethylene glycols of cholesterol; glyceryl esters; glyceryl ethers; or mixtures thereof.

0.1-3% extract from probiotic microorganisms selected from *Lactobacillus* genus, *Bifidobaceterium* genus, or mixtures thereof, 0.1-10% of humectants selected from polyhydric alcohols, alkylene glycols or glycerin, butylene glycol, hexylene glycol, propanediol, or mixtures thereof.

Even more preferred is where the skin care product comprises:

20-99% water, 0.1-5% one or more surfactants selected from PEG-60, PEG-75, PPG-5-Ceteth-20, Methyl gluceth-20, Bis-PEG-18 methyl ether dimethyl silane, Glycereth-26, Oleth-3 phosphate, Oleth-3, Oleth-5, Choleth-24, Ceteth-24, PEG-20 methyl glucosesesquiisostearate, and mixtures thereof;

0.1-3% extract from probiotic microorganisms selected from *Lactobacillus* genus, *Bifidobaceterium* genus in the form of a ferment or ferment lysate, or mixtures thereof, 0.1-10% of humectants selected from polyhydric alcohols, alkylene glycols or glycerin, butylene glycol, hexylene glycol, propanediol, or mixtures thereof.

In the method of the invention, the products may be applied in either order. Specifically, the watery lotion may be applied first, followed by application of the second skin care product or vice versa. The products both improve the efficacy of each other, such that the efficacy of the watery lotion is improved when combined with the other skin care product, and the other skin care product efficacy is improved when combined with the watery lotion. The efficacies that may be improved include increased water retention in skin.

The invention will be further described in connection with the following examples which are set forth for the purposes of illustration only.

Example 1

A watery lotion formula was prepared as follows:

| Ingredient | % by weight |
| --- | --- |
| Water | QS100 |
| Caffeine | 0.05 |
| Betaine (surfactant) | 1.00 |
| Trehalose (viscosity modifier) | 0.50 |
| Carbopol (viscosity modifier) | 7.00 |
| Tromethane | 0.13 |
| PEG-75 (surfactant) | 3.00 |
| *Bifida* ferment lysate | 5.00 |
| Acetyl glucosamine | 0.50 |
| *Lactobacillus* ferment | 1.00 |
| Spring (mineral) water (TRC Nutritional Laboratories - 77LPPM TRC Minerals) | 0.10 |
| Acetyl hexpeptide-8 (peptide) | 0.10 |
| Butylene glycol (humectants) | 0.50 |
| Hyaluronic acid (humectant) | 0.05 |
| Pentylene glycol (humectant) | 1.00 |
| Propanediol (humectant) | 2.00 |
| *Anthemis nobilis* (Chamomile) extract (botanical extract) | 0.002 |
| PPG-5-Ceteth-20 (non-ionic surfactant) | 0.12 |
| Butylene glycol (humectants) | 1.00 |

The composition was prepared by combining the ingredients and mixing well to emulsify.

Example 2

The watery lotion of Example 1 was tested along with a commercially available skin serum formula ("Test Formula" or "TF") with the ingredient labeling on the product as set forth below:
WATER\AQUA\EAU; *BIFIDA* FERMENT LYSATE; METHYL GLUCETH-20; PEG-75; BIS-PEG-18 METHYL ETHER DIMETHYL SILANE; BUTYLENE GLYCOL; PROPANEDIOL; COLA ACUMINATA (KOLA) SEED EXTRACT; ECHINACEA PURPUREA (CONEFLOWER) EXTRACT; *ANTHEMIS NOBILIS* (CHAMOMILE); HYDROLYZED ALGIN; PANTETHINE; CAFFEINE; LECITHIN; ETHYLHEXYLGLYCERIN; SODIUM RNA; BISABOLOL; GLYCERETH-26; SQUALANE; SODIUM HYALURONATE; OLETH-3 PHOSPHATE; CAPRYLYL GLYCOL; *LACTOBACILLUS* FERMENT; OLETH-3; OLETH-5; YEAST EXTRACT\FAEX\EXTRAIT DE LEVURE; CHOLETH-24; HYDROGENATED LECITHIN; CETETH-24; TOCOPHERYL ACETATE; ETHYLHEXYL METHOXYCINNAMATE; HEXYLENE GLYCOL; CARBOMER.

EFT (Epidermal Full Thickness)-300 skin models were dispensed into 6 well plates and maintained in incubator at 37° C. Daily for 48 hours wells were treated with 5 ml EFT-300 Media (Mattek) and (1) 20 uL of Test Formula ("TF"); or (2) 20 uL of watery lotion of Example 1; or (3) 20 uL of watery lotion applied for 1 hour followed by application of 20 uL of Test Formula; or (4) Untreated control.

Skins were fixed in 5% formalin for 24 hours at 4° C., embedded in paraffin and sectioned at 5 uM. Sections were stained with hematoxylin & eosin (H&E) stain to highlight overall morphology. In addition, other sections were treated with green (anti-Ki67) stain and red (anti-caspase 3) stain from Biocare Medical to identify proliferating or apoptotic cells respectively. Antibodies for filaggrin, involucrin, and transglutaminase were purchased from Abcam® sections were exposed to antibodies to quantify the degree of cellular differentiation in the histological sections. Photographic images were taken at 40×. Scale bars are 0.05 mm. The results are set forth in FIG. 1.

In reviewing histological sections, it is the basal layer where cellular proliferation takes place. As these newly proliferated cells are pushed to the epidermal layer they differentiate. In healthy skin the basal and epidermal layers must both show an appropriate mix of proliferation and differentiation that should be balanced. Cellular proliferation in the basal layer often decreases with age. As a result, cellular proliferation and differentiation in skin tends to diminish with age. Skin "lasts longer" and it often shows in the visual appearance of skin. In order for skin to appear most youthful and healthy skin renewal should be at the same or similar level that is found in young people.

The untreated control H&E and Ki-67 Caspase stained sections shows a basal to epidermal ratio of about 50:50. The basal skin layer shows cellular proliferation. The upper, epidermal layer is somewhat disrupted, but shows that cellular differentiation has occurred.

Skin sections treated with Test Formula show an increased basal layer that indicates that such treatment caused increased cellular proliferation in the basal layer. The epidermal layer is decreased in thickness compared to the untreated control, showing that the Test Formula appears to have somewhat of an inhibitory effect on the epidermal, differentiating, skin layer.

Skin sections treated with the watery lotion of Example 2 ("WL") shows that the epidermal layer increases significantly, and the basal layer decreases. This indicates that watery lotion appears to promote cellular differentiation in the epidermal layer, and has somewhat of an inhibitory effect on cellular proliferation in the basal layer.

Skin sections treated with the combination of watery lotion+Test Formula show an even mix of basal and epidermal skin layers with good integrity. The sequential or layered application of the two products promotes balanced cellular proliferation in the basal layer and cellular differentiation in the epidermal layer. Most unexpectedly, the inhibitory effect of the Test Formula on cellular differentiation and the inhibitory effect of watery lotion on cellular proliferation appears to be negated with the sequential combination of the two products. Both the basal and epidermal layers are compact, adherent, and histologically show a cohesive barrier.

Figure 2:
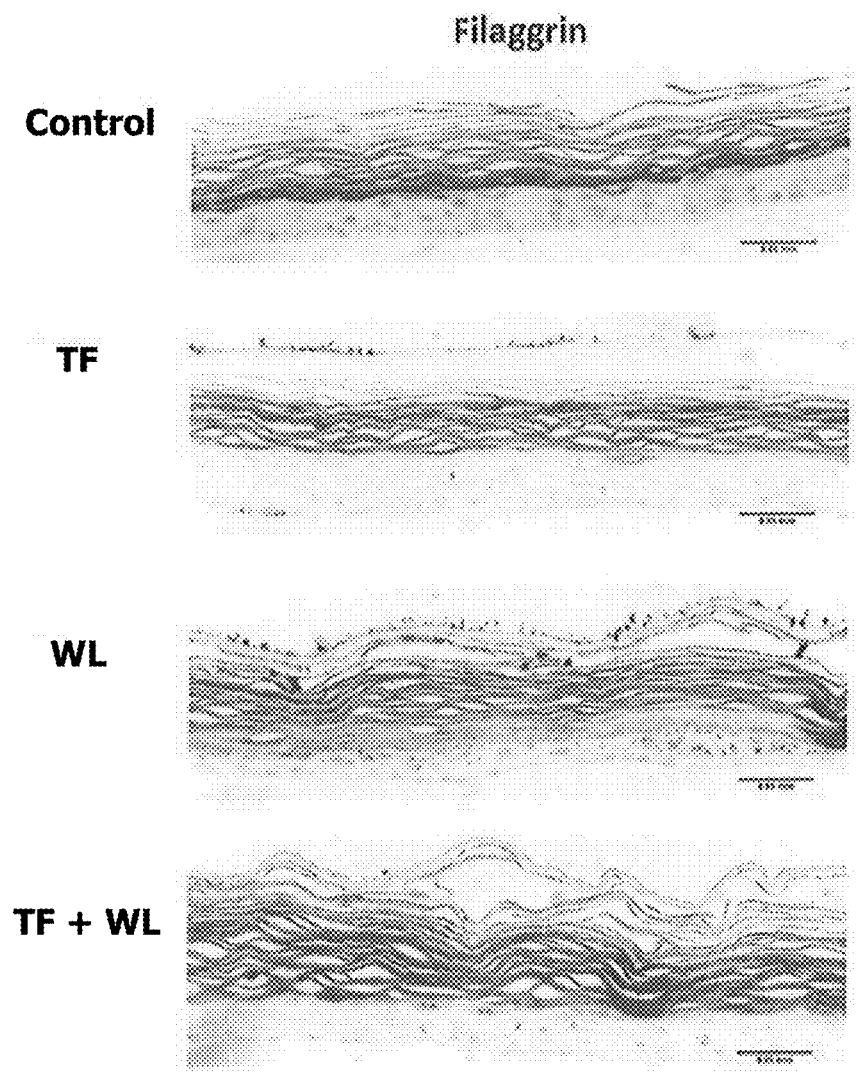
FIG. 2: depicts histological sections of untreated skin and skin treated with watery lotion alone, a skin care product ("Test Formula" or "TF"), and the combination of the watery lotion and the skin care product, stained to show cellular differentiation in the epidermal skin layer. Similar to the results in FIG. 1, the sections treated with watery lotion and the second skin care product show balanced skin renewal.

FIG. 2 shows skin sections marked for the presence of filaggrin, which is another marker for cellular differentiation.

The skin section showing untreated control demonstrates a differentiated, but somewhat disrupted epidermal layer.

Skin section "Test Formula" shows that the application of the Test Formula reduces the differentiated layer in the skin, thus apparently having a slightly inhibitory effect on cellular differentiation.

The skin section "WL" shows an increased epidermal layer demonstrating that the watery lotion does increase cellular differentiation in the basal layer.

The skin section "Test Formula+WL" shows that the sequential or combined application of Test Formula and WL shows more than an additive effect in increasing cellular differentiation in the epidermal layer in spite of the fact that one of the products (Test Formula) is shown to have an inhibitory effect on cellular differentiation in the basal layer.

Example 3

The composition and method of the invention was further tested to demonstrate increased water retention in skin using the product combination of the invention.

EFT-300 skin models were treated apically with samples alone or layered at day 0 and basal with 3 ml Media in a 6 well plate and incubated at 37° C. Samples were untreated control, Test Formula from Example 2 and Watery lotion formula of Example 1 ("WL").

Figure 3:
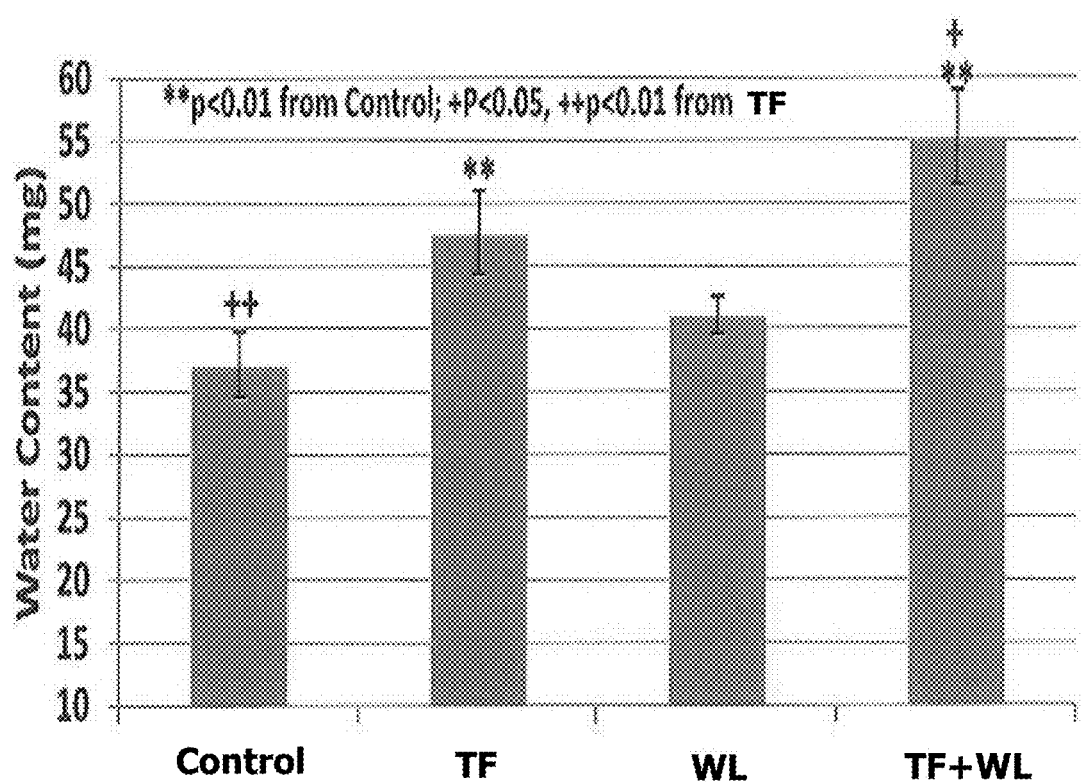
FIG. 3: depicts the increase in water content of skin treated with the combination of a watery lotion and a second skin care product when compared to skin treated with each product alone and untreated skin.

After 24 hours the skins were placed in a MatTek permeation device and treated apically with 200 μl of 100 ppm fluorescein in phosphate buffered saline. After 24 hours of fluorescein penetration skins were washed in PBS, weighed wet, then dried for 24 hours and re-weighed. Data was analyzed using one way analysis of variance (ANOVA) and significant means were tested using a Dunnet's multiple comparison post test using GraphPad Instat software. The results are set forth in FIG. 3, and show that skin samples treated with the combination of watery lotion of Example 1 and the Test Formula of Example 2 exhibit substantially improved water content retention in skin when compared to control and each product used separately.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for improving balanced skin renewal comprising layering effective amounts of a watery lotion and second skin care product on to skin in need thereof;
    wherein the watery lotion comprises:
        80 to 99.9% by weight of water,
        at least one extract from the fermentation of the microorganism *Bifidobacterium*,
        and at least one extract from the fermentation of the microorganism *Lactobacillus*,
        wherein from 0.01 to 100% of the water present in the composition is mineral water having at least 250 ppm of total mineral dissolved solids; and
    wherein the second skin care product comprises:
        20-99% water,
        0.1-5% of one or more surfactants selected from the group consisting of: alkylene glycols; alkoxylated glucose, alkoxylated alcohols, glyceryl esters, glyceryl ethers, or mixtures thereof,
        0.1-3% of an extract from probiotic microorganisms selected from *Lactobacillus* genus, *Bifidobacaterium* genus, or mixtures thereof, and
        0.1-10% of humectants selected from the group consisting of: polyhydric alcohols, alkylene glycols, glycerin, butylene glycol, hexylene glycol, or mixtures thereof.

2. The method of claim 1 wherein the balanced skin renewal is shown by skin having basal and epidermal layers showing a ratio of 30-70% basal cell layer and 30-70% epidermal layer.

3. The method of claim 1 wherein the balanced skin renewal is shown by skin having basal and epidermal layers showing a ratio of 40-60% basal layer and 60-40% of differentiated layer.

4. The method of claim 1 wherein the balanced skin renewal is shown by skin having about 50% basal layer and about 50% epidermal layer.

5. The method of claim 1 wherein the second skin care product comprises:
    20-99% water,
    0.1-5% one or more surfactants selected from PEG-60, PEG-75, PPG-5-Ceteth-20, Methyl gluceth-20, Bis-PEG-18 methyl ether dimethyl silane, Glycereth-26, Oleth-3 phosphate, Oleth-3, Oleth-5, Choleth-24, Ceteth-24, PEG-20 methyl glucosesesquiisostearate, and mixtures thereof;
    0.1-3% extract from probiotic microorganisms selected from *Lactobacillus* genus, *Bifidobaceterium* genus in the form of a ferment or ferment lysate, or mixtures thereof,
    0.1-10% of humectants selected from polyhydric alcohols, alkylene glycols or glycerin, butylene glycol, hexylene glycol, propanediol, or mixtures thereof.

6. The method of claim 5 wherein the second skin care product comprises:
    20-99% water,
    0.1-5% one or more surfactants selected from PEG-60, PEG-75, PPG-5-Ceteth-20, Methyl gluceth-20, Bis-PEG-18 methyl ether dimethyl silane, Glycereth-26, Oleth-3 phosphate, Oleth-3, Oleth-5, Choleth-24, Ceteth-24, PEG-20 methyl glucosesesquiisostearate, and mixtures thereof;
    0.1-3% extract from probiotic microorganisms selected from *Lactobacillus* genus, *Bifidobaceterium* genus in the form of a ferment or ferment lysate, or mixtures thereof,
    0.1-10% of humectants selected from polyhydric alcohols, alkylene glycols or glycerin, butylene glycol, hexylene glycol, propanediol, or mixtures thereof.

7. The method of claim 1 wherein the extract from the fermentation of the microorganism *Bifidobacterium* in the watery lotion is *Bifida* ferment extract, *Bifida* ferment lysate, *Bifida* ferment filtrate, or mixtures thereof.

8. The method of claim 1 wherein the extract from the fermentation of *Lactobacillus* in the watery lotion is a ferment extract, ferment lysate, or ferment filtrate.

9. The method of claim 1 wherein the extract from the fermentation of *Lactobacillus* in the watery lotion is from one or more of the species *plantarum, casei,* or *crispatus*.

10. The method of claim 1 wherein the mineral water has a pH ranging from 2.5 to 4.3, and a specific gravity of 1.0 to 1.03.

* * * * *